(12) United States Patent
Dieckgraefe et al.

(10) Patent No.: US 7,060,262 B2
(45) Date of Patent: Jun. 13, 2006

(54) STIMULATING NEUTROPHIL FUNCTION TO TREAT INFLAMMATORY BOWEL DISEASE

(75) Inventors: Brian K. Dieckgraefe, Chesterfield, MO (US); Joshua Korzenik, St. Louis, MO (US)

(73) Assignee: The Washington University, St. Louis, MO (US)

( * ) Notice: Subject to any disclaimer, the term of this patent is extended or adjusted under 35 U.S.C. 154(b) by 163 days.

(21) Appl. No.: 10/260,354

(22) Filed: Oct. 1, 2002

(65) Prior Publication Data

US 2003/0035801 A1 Feb. 20, 2003

Related U.S. Application Data

(60) Division of application No. 09/637,062, filed on Aug. 11, 2000, now Pat. No. 6,500,418, which is a continuation-in-part of application No. 09/502,047, filed on Feb. 11, 2000, now abandoned.

(60) Provisional application No. 60/119,842, filed on Feb. 12, 1999.

(51) Int. Cl.
*A61K 45/00* (2006.01)
*A61K 39/395* (2006.01)
*A61K 39/19* (2006.01)

(52) U.S. Cl. ............... 424/85.2; 424/85.1; 424/145; 514/8; 514/12; 514/893

(58) Field of Classification Search ............... 424/85.2, 424/85.1, 145; 514/8, 12, 893
See application file for complete search history.

(56) References Cited

U.S. PATENT DOCUMENTS

| | | | |
|---|---|---|---|
| 4,961,926 A | 10/1990 | Gabrilove | |
| 5,284,656 A | 2/1994 | Platz et al. | |
| 5,468,846 A | 11/1995 | Ichikawa et al. | |
| 5,606,024 A | 2/1997 | Boone et al. | |
| 5,654,186 A | 8/1997 | Cerami | |
| 5,762,920 A | 6/1998 | Yung et al. | |
| 5,767,156 A | 6/1998 | Ferrante et al. | |
| 5,790,421 A | 8/1998 | Osslund | |
| 5,814,308 A | 9/1998 | Zhang | |
| 6,020,469 A | 2/2000 | Hershenson | |
| 6,037,324 A | 3/2000 | Schwender et al. | |

FOREIGN PATENT DOCUMENTS

| | | |
|---|---|---|
| WO | WO 00 06080 A | 2/2000 |
| WO | WO 00 47195 A | 8/2000 |

OTHER PUBLICATIONS

Roe et al. Brief Report: treatment of Chronic Inflammation Bowel Disease in Glycogen Storage Disease Type Ib with Colony Stimulating Factors. The New England Journal of Medicine, vol. 326, No. 25, pp. 1666-1992.*
B. Drumm et al., "Granulocyte-macrophage colony-stimulating factor for Crohn's disease", *The Lancet*, (May 24, 2003) vol. 361, pp. 1830-1831.
B. Dieckgraefe et al. "Authors Reply", *The Lancet*, (May 24, 2003) vol. 361, pp. 1830-1831.
D. Vaughn et al., "Treatment of Fistulas with Granulocyte Colony-Stimulating Factor in a Patient with Crohn's Disease", *N.E.J.M.* (1999) vol. 340, pp. 239-240.
J. R. Korzenik et al., "Immunostimulation in Crohn's disease: Results of a pilot study of G-CSF (R-MethuG-SCF) in mucosal and fistulizing Crohn's disease", *Gastroenterology*, (Apr. 2000) vol. 118, No. 4, Suppl. 2, part 1, pp. A874-A875 Abstract nr 4852.
J.R. Korzenik et al., "Is Crohn's disease an immunodeficiency? A hypothesis suggesting possible early events in the pathogenesis of Crohn's disease", *Digestive Diseases and Sciences* (Jun. 2000) vol. 45, No. 6, pp. 1121-1129.
C.J. Bagley et al., "The structural and functional basis of cytokine receptor activation: Lessons from the common beta subunit of the granulocyte-macrophage colony-stimulating factor, interleukin-3 (IL-3), and IL-5 receptors", *Blood*, (Mar. 1, 1997), vol. 89, No. 5, pp. 1471-1482.
J. R. Korzenik et al., "Immune stimulation in Crohn's disease: Safety and efficacy of rbuGM-CSF for the treatment of active Crohn's disease" *Gastroenterology*, (Apr. 2001) vol. 120, No. 5, Suppl. 1, pp. A277-278 Abstract nr. 1437.
R. Leake, "Molecular Aspects of the GM-CSF Receptor: An Example of the Cell Signalling Mechanism Used by Type 1 Cytokine Receptors", European Journal of Cancer, vol. 35, Supp. 3, pp. S2-S3, 1999.
Roe et al. "Treatment of Chronic Inflammatory Disease in Glycogen Storage Disease Type 1 b with GM-CSF," *The New England Journal of Medicine*, (1992), pp. 1666-1669, vol. 326, No. 25.

* cited by examiner

*Primary Examiner*—Eileen O'Hara
*Assistant Examiner*—Fozia Hamud
(74) *Attorney, Agent, or Firm*—Banner & Witcoff, Ltd.

(57) ABSTRACT

Immune stimulatory amounts of hematopoietic colony stimulating factors are administered to patients with inflammatory bowel disease. The factors include G-CSF and GM-CSF. These factors induce and maintain remission of the disease and its manifestations, whether within the intestine or without.

20 Claims, 2 Drawing Sheets

FIG. 1

| | WEEK OF THERAPY | | | | | | | RESPONSE OR REMISSION |
|---|---|---|---|---|---|---|---|---|
| | 0 | 1 | 2 | 4 | 6 | 8 | 10 | 12 | |
| A | 273 | 269 | 306 | 310 | 251 | 170 | 239 | 109 | ✓ |
| B | 337 | 288 | 265 | 221 | 279 | 248 | 290 | 164 | ✓ |
| C | 258 | 257 | 211 | 108 | 73 | 36 | 74 | 163 | ✓ |
| D | 428 | 281 | 255 | 127 | 220 | 260 | 207 | 212 | ✓ |
| E | 248 | 222 | 130 | 68 | 6 | 80¹ | | | ✓ |
| F | 285 | 356 | 416 | | | | | | |
| G | 248 | 305 | 398 | 308 | 417 | | | | |
| H | 234 | 157 | 165 | 188 | 205 | 299 | 96 | 147 | ✓ |
| I | 212 | 264 | 282 | 238 | 178 | 160 | 154² | | |
| J | 330 | 211 | 182 | 159 | 265 | 225 | 206³ | | ✓ |
| K | 241 | 301 | 280 | 271 | 305 | 265 | 217 | 204 | |
| L | 306 | 303 | 270 | 284 | 344 | 285 | 312⁴ | | |
| M | 368 | 358 | 326⁵ | | | | | | |
| N | 268 | 189 | 136 | 65 | 105 | 98 | | | ✓ |
| O | 382 | 397 | 263 | 272 | 279 | 344 | 288 | | ✓ |
| P | 344 | 463 | | | | | | | ✓ |
| Q | 288 | 163 | 165 | 174 | 164 | 181 | | | ✓ |

ACTIVE  RESPONSE  REMISSION  DISCONTINUE (1) FISTULAS CLOSED, TREATMENT ENDS AT 8 WEEKS PER PROTOCOL,
(2) PARTIAL SMALL BOWEL OBSTRUCTION, (3) PERIANAL ABSCESS DRAINAGE
(4) PATIENT REQUESTED CHANGE OF THERAPY, (5) TAKEN OUT OF PROTOCOL FOR CONCURRENT ILLNESS

STIMULATING NEUTROPHIL FUNCTION TO TREAT INFLAMMATORY BOWEL DISEASE

This application is a divisional of prior U.S. patent application Ser. No. 09/637,062 filed Aug. 11, 2000 now U.S. Pat. No. 6,500,418, which is a continuation-in-part of application Ser. No. 09/502,047 filed Feb. 11, 2000 now abandoned, which claims the benefit of Provisional Application Ser. No. 60/119,842 filed Feb. 12, 1999. The disclosure of the provisional application is expressly incorporated by reference herein.

BACKGROUND OF THE INVENTION

Crohn's disease persists as an enigma: without a deciphered etiology and without adequate therapy. Prevailing explanations of the pathogenesis of Crohn's disease (Crohn's Disease) hold that the characteristic chronic intestinal inflammation results from an aberrant, activated immune response generated against ubiquitous bacteria or bacterial products that gain access to the lamina propria, perhaps through a more permeable intestinal barrier. The abnormal reaction has been suggested to be mediated principally by T-cells enhanced by an intrinsic imbalance in pro-inflammatory and contra-inflammatory mediators. Thus, most therapy aims to counteract that inflammatory state with increasingly potent and sophisticated immune suppressants.

Current therapy, mostly directed at suppressing the inflammatory process, remains inadequate both for the treatment of flares and maintenance of remission. Steroids can be effective in short term use but produce dependency in a significant proportion of patients. While certain antibiotics appear promising, data are limited. Thus there is a need in the art for effective method for treating inflammatory bowel diseases.

SUMMARY OF THE INVENTION

It is an object of the invention to provide a method of treating Crohn's Disease.

It is an object of the invention to provide a method of treating Ulcerative Colitis.

It is another object of the invention to provide a method of treating extrainstestinal manifestations of Ulcerative Colitis or Crohn's disease.

It is still another object of the invention to provide a method of treating pouchitis.

It is yet another object of the invention to treat and reduce the risk of fistula recurrence.

These and other objects of the invention are provided by one or more of the embodiments described below. In one embodiment a method is provided of treating Crohn's Disease in which an immune stimulatory amount of an agonist of CD114 (Granulocyte Colony Stimulating Factor Receptor (G-CSFR)) is administered to a patient with Crohn's Disease not associated with Glycogen Storage Disease 1b.

In another embodiment of the invention another method of treating Crohn's Disease is provided. An immune stimulatory amount of an agonist of CD116 (Granulocyte-Macrophage Colony Stimulating Factor Receptor) or CDw131 is administered to a patient with Crohn's Disease not associated with Glycogen Storage Disease 1b.

In yet another embodiment of the invention another method is provided of treating Crohn's Disease. An immune stimulatory amount of an agonist of CD114 (Granulocyte Colony Stimulating Factor Receptor (G-CSFR)) is administered to a patient with Crohn's Disease not associated with Chronic Granulomatous Disease.

In still another embodiment of the invention a method is provided of treating Crohn's Disease in which an immune stimulatory amount of an agonist of CD116 (Granulocyte-Macrophage Colony Stimulating Factor Receptor) or CDw131 is administered to a patient with Crohn's Disease not associated with Chronic Granulomatous Disease.

In even another embodiment of the invention another method is provided of treating Crohn's Disease. An immune stimulatory amount of an agonist of CD114 (Granulocyte Colony Stimulating Factor Receptor (G-CSFR)) is administered to a patient with Crohn's Disease not associated with a presently characterized and identifiable specific neutrophil disorder caused by a genetic disease.

In yet another embodiment of the invention another method is provided of treating Crohn's Disease. An immune stimulatory amount of an agonist of CD116 (Granulocyte-Macrophage Colony Stimulating Factor Receptor) or CDw131 is administered to a patient with Crohn's Disease not associated with a presently characterized and identifiable specific neutrophil disorder caused by a genetic disease.

According to another aspect of the invention a method is provided of treating Ulcerative Colitis. An immune stimulatory amount of an agonist of CD114 (Granulocyte Colony Stimulating Factor Receptor (G-CSFR)) is administered to a patient with Ulcerative Colitis.

According to another aspect of the invention a method is provided of treating Ulcerative Colitis. An immune stimulatory amount of an agonist of CD116 (Granulocyte-Macrophage Colony Stimulating Factor Receptor) or CDw131 is administered to a patient with Ulcerative Colitis.

Another aspect of the invention is a method of treating extraintestinal manifestations of Ulcerative Colitis. An immune stimulatory amount of an agonist of CD114 (Granulocyte Colony Stimulating Factor Receptor (G-CSFR)) is administered to a patient with extraintestinal manifestations of Ulcerative Colitis.

Another aspect of the invention is a method of treating extraintestinal manifestations of Ulcerative Colitis. An immune stimulatory amount of an agonist of CD116 (Granulocyte-Macrophage Colony Simulating Factor Receptor) or CDw131 is administered to a patient with extraintestinal manifestations of Ulcerative Colitis.

According to still another aspect of the invention a method is provided of treating pouchitis. An immune stimulatory amount of an agonist of CD114 (Granulocyte Colony Stimulating Factor Receptor (G-CSFR)) is administered to a patient with pouchitis.

According to still another aspect of the invention a method is provided of treating pouchitis. An immune stimulatory amount of an agonist of CD116 (Granulocyte-Macrophage Colony Stimulating Factor Receptor) or CDw131 is administered to a patient with pouchitis.

According to still another aspect of the invention a method is provided of preventing or reducing the risk of fistula recurrence. An immune stimulatory amount of an agonist of CD114 (Granulocyte Colony Stimulating Factor Receptor (G-CSFR)) is administered to a patient with Crohn's disease who has previously had a fistula, whereby the risk of recurrence of a fistula is reduced According to still another aspect of the invention a method is provided of preventing or reducing the risk of fistula recurrence. An immune stimulatory amount of an agonist of CD116 (Granulocyte-Macrophage Colony Stimulating Factor Receptor) or CDw131 is administered to a patient with Crohn's disease who has previously had a fistula, whereby the risk of recurrence of a fistula is reduced.

The present invention thus opens a new realm of treatment modalities for inflammatory bowel diseases which have proven refractory to discovery of safe and effective ministrations. Contrary to the prior paradigm in the art of treating inflammatory bowel diseases with immunosuppressive agents, the present invention uses agents known to be immunostimulatory to treat, prevent, and maintain remission of such diseases.

BRIEF DESCRIPTION OF THE DRAWINGS

FIG. 1 shows the response of 17 patients to a 12-week regimen of therapy with G-CSF.

DETAILED DESCRIPTION OF THE INVENTION

Figure 2:
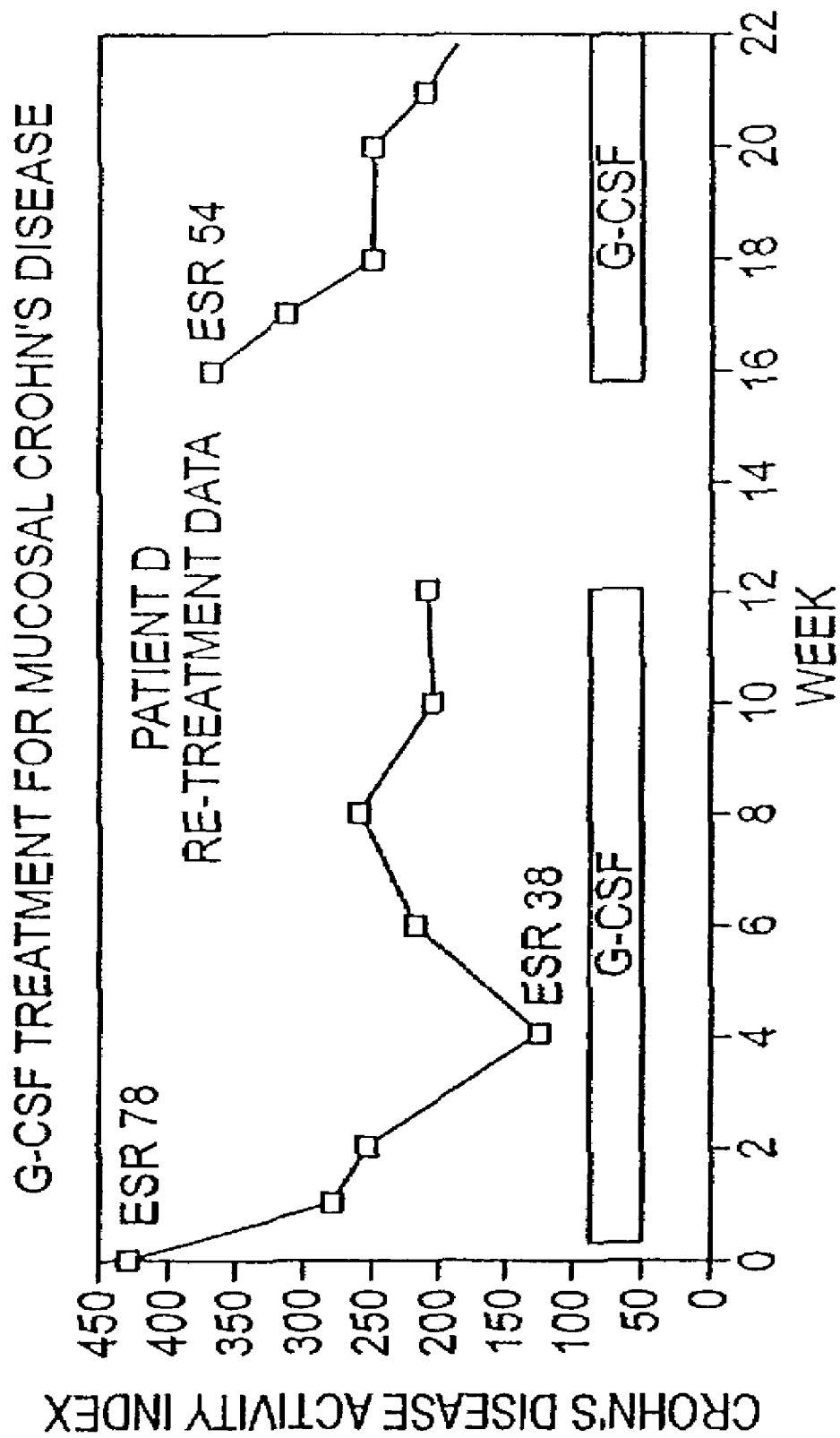
FIG. 2 shows the response of patient D during treatment and retreatment.

It is a discovery of the present inventors that immune modulatory factors which act at CD114, CD116, and or CDw131 can be successfully used to treat various forms of inflammatory bowel disease. These include but are not limited to Crohn's Disease, with or without a presently characterized and identifiable specific neutrophil disorder (such as Glycogen Storage Disease 1b or Chronic Granulomatous Diseases) pouchitis, fistulas, extraintestinal manifestations of Crohn's Disease, and Ulcerative Colitis. The Ulcerative Colitis can be of any extent, including proctitis, proctosigmoiditis, left-sided colitis, or pan-colitis.

The immune modulatory factor can be any which binds to CD114, CDw131, or CD116, including G-CSF, GM-CSF, IL-3, IL-5, and peptidomimetics or non-peptidomimetics of these factors which induce tyrosine phosphorylation of multiple signaling proteins, which stimulate primary bone marrow cells to form granulocytic colonies in vitro, and/or which elevate peripheral blood neutrophil counts. Nartograstim, myelopoietins, circularly permuted G-CSF sequences, SB247464 are among the known mimetics of G-CSF. See, McWherter et al., Biochemistry 14:4564–71, 1999; Feng et al., Biochemistry 14:4553–63, 1999; Tian et al., Science 281:257–59,1998; and Kuwabara et al., Am. J. Physiology 271:E73–84, 1996. M-CSF may also be used in accordance with the present invention. The agonist may be administered as is known in the art. Typically this will be by subcutaneous injection or intravenous infusion, however other methods such as oral, intraperitoneal, subdermal, and intramuscular administrations can be used. Doses which are delivered may be the same as those which are delivered to stimulate an immune response in humans for other disease purposes. Typically doses of the factors will be between about 0.1 and 100 μg/kg of body weight per day. More preferably this will be between about 1.0 and 10 μg/kg of body weight per day. Most preferably the dose will be between about 2 and 8 μg/kg of body weight per day. Corresponding amounts of peptidomimetics and non-peptidomimetics to achieve the same activity can be used. White blood cell counts can be monitored to maintain a value in the range of 10 and 60.

The immune modulatory factors are typically growth factors or colony stimulating factors which affect the growth of hematopoietic cells, particularly myeloid cells, including polymorphonuclear leukocytes, monocytes, and macrophages. Such factors include but are not limited to myeloid cell stimulatory factors, polymorphonuclear leukocyte stimulatory factors, and granulocytic cell stimulatory factors. Particularly useful factors are GCSF, GMCSF, and MCSF. Any form of such factors known in the art can be used. The form may be an isoform or a differently post-translationally modified form of the factor. The factor may be one which is isolated from humans or other primates or mammals. The factor may be one which is made in a recombinant organism, from bacteria to yeast to sheep.

Diseases which are amenable to treatment as described herein include all within the umbrella of inflammatory bowel disease. The phrase "Crohn's Disease not associated with disease X" as used here means that the patient that is being treated according to the method of the invention has not been diagnosed with disease X. Presently characterized and identifiable specific neutrophil disorders caused by genetic diseases include Chronic Granulomatous Disease, Glycogen storage disease 1b, leukocyte adhesion deficiency, Turner's syndrome, Chediak-Higashi, myeloproliferative disease, neutropenias of various causes, and myelodysplastic disease. Ulcerative colitis can be manifested as proctosigmoiditis, left-sided colitis, or pan-colitis. All of these are included in the term "Ulcerative colitis". Pouchitis is an inflammation of an surgically created pouch in the gastrointestinal tract.

One goal of treatment is the amelioration, either partial or complete, either temporary or permanent, of patient symptoms, including inflammation of the mucosa, extraintestinal manifestations of the disease, or epithelial damage. Any amelioration is considered successful treatment. This is especially true as amelioration of some magnitude may allow reduction of other medical or surgical treatment which may be more toxic or invasive to the patient. Extraintestinal disease manifestations include those of the liver, bile duct, eyes, and skin. Another goal of the treatment is to maintain a lack of excess intestinal inflammation in persons who have already achieved remission.

The present invention is based on the theory that the fundamental immune dysregulation of Crohn's Disease results not from an excessive immune response but from a primary immune deficiency. This deficiency likely results from genetic variations in neutrophil and/or macrophage phenotypes interacting with a discrete set of bacteria which suppress neutrophil/macrophage function. In turn, this deficiency provokes a broader compensatory response, amplifying inflammation, activating lymphocytes, culminating in Crohn's Disease.

The recent account of patients experiencing prolonged remission after allogeneic bone marrow transplant (BMT) suggests that the marrow phenotype may be central to the pathogenesis of Crohn's Disease. Five patients with Crohn's Disease and chronic myelogenous leukemia underwent BMT with recurrence of Crohn's Disease in only one patient who remained chimeric with native and transplanted marrow. Conversely, the recurrence of Crohn's Disease in transplanted small bowel reinforces the idea that a critical factor in the development of Crohn's Disease may be extraintestinal, perhaps partly an intrinsic marrow defect, and that Crohn's Disease is not an inherent intestinal abnormality. Consequently, Crohn's Disease ought to be considered not as a disease of primary intestinal dysfunction but the result of an interaction between marrow constituents and the intestinal environment.

Several genetic syndromes with which Crohn's Disease has been associated provide insight into the possible marrow defects of Crohn's Disease. In particular, five genetic diseases can present with a clinical/histopathological process indistinguishable from Crohn's Disease: chronic granulomatous disease, glycogen storage disease Ib, Leukocyte Adhesion Deficiency, Chediak-Higashi syndrome and Turner's syndrome. A distinct deficiency in neutrophil function has been described in each of these syndromes. In addition, Crohn's Disease has been described in association with congenital, autoimmune, and cyclic neutropenias, familial Mediterranean fever, myelodysplastic, and myeloproliferative diseases. The diagnosis of leukemia preceded Crohn's Disease in nearly half the cases in the largest series and diagnosis of myelodysplasia and Crohn's Disease was made concomitantly in half the subjects in another study suggesting a possible causal relationship for the development of Crohn's Disease initiated by an accumulation of dysfunctional neutrophils. These syndromes provide evidence that a variety of functional neutrophil deficiencies can result in a pathophysiology indistinguishable from Crohn's Disease. Disorders of neutrophil/macrophage function represent a potential starting point for understanding Crohn's Disease.

A role for intestinal flora has been established in Crohn's Disease. Reinforced by other evidence, the importance of the microflora has been demonstrated by the provocation of inflammation with the direct introduction of ileostomy output into a defunctionalized intestinal segment while a sterile, filtered fraction fails to induce disease activity. While this response is considered non-specific to ubiquitous bacteria, specific alterations in the fecal flora have been identified in patients with Crohn's Disease compared to healthy controls. In Crohn's Disease, *Bacteroides* tend to be present in increased amounts while *Lactobacillus* and *Bifidobacteria* are diminished, though results of studies are not unanimous. Some *Bacteroides* species have been shown to impair phagocytosis as well as the microbicidal activity of neutrophils for aerobic bacteria. A discrete subset of the intestinal flora may be responsible for influencing neutrophil/macrophage function in Crohn's Disease. Recent work with animal models of IBD also support a protective role for *Lactobacillus* and *Bifidobacteria* which may act to counter effects of other bacteria and stimulate immune function. The ratio between these different classes of bacteria may be the critical factor in maintaining intestinal health in a susceptible subgroup. Consequently, as suggested by periodontitis, it is unlikely that a single bacteria would be demonstrated as the sole causative agent in Crohn's Disease; instead, these data highlight the complexity of bacterial-immune interactions. The localized nature of the interaction between specific bacteria and leukocytes would account for the specific intestinal manifestations, rather than more systemic findings.

Any explanation of the Crohn's Disease must account for the disease as a twentieth century phenomena in industrialized countries. The disease appears at best rare before Crohn's defining publication in 1932. One possible, relevant, radical change in the past half century may be a shift in intestinal flora. Twentieth century innovations in food preservation with the introduction of refrigeration and other techniques may have produced a fundamental change in the type and amount of bacteria ingested, and may alter the intestinal bacterial content. In comparison to intestinal flora in rural Africa where Crohn's Disease remains rare, the gut flora of westernized countries contain higher concentrations of *Bacteroides* as well as decreased amounts of *Bifidobacteria*, perhaps predisposing the intestinal environment to impair the host immune response and set the stage, in the susceptible host, for the development of Crohn's Disease.

While the human intestinal bacterial flora resists alteration, it can be manipulated. Once established in infancy, the bacterial flora undergoes some changes after weaning but remains remarkably constant throughout life. The protective role of breast feeding against the development of Crohn's Disease may be through promoting *Bifidobacteria* in higher concentrations and limiting *Bacteroides*, an effect which has been well documented. The demonstrated association of increased refined carbohydrate intake with Crohn's Disease may be explained through its influence on gut flora as well.

While a change in flora in the susceptible host may alone be sufficient and an important result of the westernized lifestyles, other factors are likely contributory. The rise in the latter half of this century of smoking and non-steroidal anti-inflammatory drug (NSAID) use, risk factors for Crohn's Disease, may be in part responsible for the increase in Crohn's Disease, though the nature of their influence on the pathophysiology remains uncertain. While several actions of nicotine have been advanced for its influence on Crohn's Disease, nicotine's primary detrimental effect may be on neutrophil function, an effect which has been repeatedly demonstrated. Likewise, though numerous mechanisms have also been proposed for the deleterious effects of NSAIDs on patients with IBD, NSAIDs impairment of neutrophil function may be central to their impact on Crohn's Disease. These factors, each suppressing immune function, may potentiate the same pathway and promote the development or persistence of Crohn's Disease.

The GM-CSF receptor is composed of two subunits:
1) Hs. 182378 colony stimulating factor 2 receptor, alpha, low-affinity (granulocyte-macrophage) CSF2RA (CD116)

GM-CSF receptor alpha chain

The primary binding subunit of the GM-CSF receptor.

CD116 is a Type I transmembrane protein with about 400 amino acids. Extracellular, transmembrane and cytoplasmic domains consist of 297, 27, and 54 amino acid residues, respectively. There is one unit of class I cytokine receptor motif in the extracellular domain and no intrinsic enzymatic activity in the cytoplasmic domain. A number of isoforms are generated by alternative splicing of several soluble forms. All the isoforms are relatively minor species and their physiological function if any is not known. One is a soluble form without the transmembrane domain and the second form is identical to the original one except that the last 25 amino acids of the original receptor is substituted by a 35 amino acids segment CD116 binds GM-CSF with low affinity and binds it with high affinity when it is co-expressed with the common beta subunit CDw131 (the common beta subunit (CDw131) of the GM-CSF, IL-3, and IL-5 receptors). Expression of this subunit is found in various myeloid cells including macrophages, neutrophils, eosinophils, dendritic cells and their precursors.

Tavernier et al. (1991) demonstrated that the high affinity receptor for interleukin-5 (IL5R; 147851) and the receptor for granulocyte-macrophage CSF (CSF2R; 306250) share a beta chain. The finding provides a molecular basis for the observation that IL5 (147850) and CSF2 (138960) can partially interfere with each other's binding and have highly overlapping biologic activities on eosinophils. Kitamura et al. (1991) demonstrated that the receptor for interleukin-3 (IL3RA; 308385) likewise shares a beta subunit with CSF2R.

2) Hs.265262 colony stimulating factor 2 receptor, beta, low-affinity (granulocyte-macrophage) CSF2RB*

(CDw131)

Alternate names for CDw131 are common beta subunit INTERLEUKIN 5 RECEPTOR, BETA; IL5RB INTERLEUKIN 3 RECEPTOR, BETA; IL3RB *138981 GRANULOCYTE-MACROPHAGE COLONY-STIMULATING FACTOR RECEPTOR, BETA; CSF2RB CDw131 does not bind any cytokine by itself However, it is a component of the high affinity IL-3, GM-CSF and IL-5 receptors. CDw131 is tyrosine phosphorylated upon binding of these cytokines to the high affinity receptors. JAK2 tyrosine kinase is associated with CDw131 and tyrosine phosphorylates upon stimulation. Tyrosine phosphorylated CD131 binds various signaling molecules with an SH2 domain. These include Shc, Grb2, SHP1, SHP2, P13 kinase and STAT5, making it a key signal transducing molecule of the IL-3, GM-CSF and IL-5 receptors.

The following references are expressly incorporated herein for their teachings regarding the common beta subunit of these receptors:

Dirksen, U.; Nishinakamura, R.; Groneck, P.; Hattenhorst, U.; Nogee, L.; Murray, R.; Burdach, S.: Human pulmonary alveolar proteinosis associated with a defect in GM-CSF/IL-3/IL-5 receptor common beta chain expression. J. Clin. Invest. 100: 2211–2217, 1997.

Jenkins, B. J.; D'Andrea, R.; Gonda, T. J.: Activating point mutations in the common beta subunit of the human GM-CSF, IL-3 and IL-5 receptors suggest the involvement of beta subunit dimerization and celltype-specific molecules in signalling. EMBO J. 14: 4276–4287, 1995.

Kitamura, T.; Sato, N.; Arai, K.; Miyajima, A.: Expression cloning of the human IL-3 receptor cDNA reveals a shared beta subunit for the human IL-3 and GM-CSF receptors.

EXAMPLES

Example 1

This example shows the treatment of 3 Crohn's disease patients with GM-CSF. All three meet the definition of treatment response (CDAI decrease of greater than 70). Patients 2 and 3 are very early in their treatments and it appears likely that they will go into remission. The protocol employed is described below.

| Patient 1 | | |
|---|---|---|
| Pretreatment | CDAI: | 340.4 |
| Week 1 | CDAI: | 344.4 |
| Week 2 | CDAI: | 285.6 |
| Week 3 | CDAI: | 286.6 |
| Week 5 | CDAI: | 276.4 |
| Week 6 | CDAI: | 299.4 |
| Week 8 | CDAI: | 209.2 |
| Patient 2 | | |
| Pretreatment | CDAI: | 349.6 |
| Week 1 | CDAI: | 274.0 |
| Week 2 | CDAI: | 227.0 |
| Week 3 | CDAI: | 216.6 |
| Patient 3 | | |
| Pretreatment | CDAI: | 410.8 |
| Week 1 | CDAI: | 299.0 |
| Week 2 | CDAI: | 231.4 |

Example 2

This example demonstrates the treatment of 17 Crohn's disease patients with G-CSF.

Subjects were enrolled with active disease (CDAI>200) or with active fistulous disease. Patients were not included if other immunosuppressants had been used for standard periods of time (4 weeks for steroids, azathioprine/6-MP; 3 months for infliximab) and were allowed to be on 5-ASA products (if on for at least 8 weeks and same dose for at least 4 weeks). Subjects had a complete blood count (CBC) test weekly and were examined at least every other week for Crohn's Disease activity index (CDAI) determination and/or evaluation of fistulae. FIG. 2 shows the Crohn's Disease Activity Index (CDAI) at the onset (week 0) and followed over a 12-week course of treatment. Clinical "response" in Crohn's disease protocols is typically defined as a decrease in CDAI greater than 70. Ten of the 17 patients were responders, with a mean decrease in disease activity of 140 points. Seven of the ten achieved remission. Seven non-responders, including patient M who was withdrawn early from the study for concurrent illness, had a mean increase in CDAI of 41 points. Spontaneous closure of perianal fistulas is very rare. Our cohort included three patients with perianal fistula. At completion of therapy, all three patients had fistulas which closed. Conversion of a draining fistula to an abscess (seen ~10% of the time with Infliximab treatment) occurred in one patient. This is believed to reflect closure of the fistula tract at the skin before closure of the internal opening to the intestine. Increasing disease activity in several patients as G-CSF was tapered (per original protocol), suggested the possibility of a dose response effect. Accordingly, the protocol was amended for different dosing and to permit patient re-treatment. FIG. 3 shows the overall treatment course for patient D. A dramatic improvement resulted from the initial 12 week G-CSF course, coupled with a significant decrease in erythrocyte sedimentation index (ESR, a non-specific marker for inflammation). Discontinuation of therapy between weeks 12 to 16 was associated with increasing disease activity, which again rapidly responded to reinstitution of G-CSF therapy.

Example 3

This example shows the protocol for a further study of the method of the present invention using G-CSF An open-labeled trial of G-CSF for 12 weeks for patients with active CD and/or active fistulae secondary to Crohn's disease is initiated. The trial involves two separate, interrelated protocols. In conjunction with this treatment protocol, functional neutrophil studies are performed.

Treatment of active mucosal inflammation in Crohn's disease is the primary focus of Part A. Disease activity is defined by a standard Crohn's disease activity index. Patients are enrolled if they have moderate to severe disease activity using entry criteria outlined below. The study is an open-labeled study of fifteen patients with a dose titration protocol designed to provide neutrophil functional stimulation and achieve a moderate leukocytosis. Each subject is studied for twelve weeks of every day subcutaneous administration of G-CSF. Disease activity is followed by standard CDAI, and the quality of life (IBDQ) scale. We are treating new patients (those not included in our initial study) and offer retreatment to any of the previously treated mucosa patients meeting inclusion criteria.

The primary focus of Part B is to determine the efficacy of G-CSF in patients with perianal and rectovaginal fistula associated with Crohn's disease. Perianal fistulae are common lesions in Crohn's disease and pose a serious threat to the integrity of the normal rectal sphincter. Current therapy for these lesions are suboptimal. This study is designed as an open-labeled study of fifteen patients with a dose titration protocol designed to stimulate neutrophil function and associated leukocytosis. Fistulae are assessed by photography, standard examination scoring criteria, as well as a patient subjective assessment of pain, drainage, and overall well-being. Each subject is studied for twelve weeks on daily subcutaneous G-CSF. Disease activity is also monitored by standard CDAI, and the quality of life (IBDQ) scale.

On the basis of extensive investigational and ongoing international clinical experience with G-CSF, the safety profile is well known. In addition, several patients with active Crohn's disease or Crohn's like intestinal disease have been reported in the medical literature who have been successfully treated (for coexisting disorders) with GM-CSF or G-CSF without any serious or significant adverse effects. Based on the extensive clinical experience with G-CSF and the preliminary evidence of the reported cases, no predictable risks are anticipated at the doses studied. Nevertheless, as this is a new and counterintuitive approach to a chronic inflammatory disease, we are closely monitoring patients for safety and any adverse effects during this protocol.

Treatment Groups

Part A. Treatment of moderate to severe Crohn's disease. Patients are assigned to receive a starting dose of 3.5 micrograms/kilogram/day of G-CSF as a subcutaneous bolus injection. Dosages are adjusted as outlined below, "ANC response-based dosing of G-CSF." Treatment continues for 12 weeks. CDAI is calculated at enrollment, at the start of therapy, and every other week. The Inflammatory Bowel Disease Quality of Life Survey is completed initially and at weeks four, eight, twelve, and sixteen. Follow-up is performed at week 16 with telephone follow-up monthly out to six months from the date of enrollment or up to relapse.

Part B. Treatment of perianal and rectovaginal fistula in Crohn's disease. Patients are assigned to receive a starting dose of 3.5 micrograms/kilogram/day of G-CSF as a subcutaneous bolus injection. Dosages are adjusted as outlined below—"ANC response-based dosing of G-CSF." Patients who have closed all fistulae before week 8, have G-CSF therapy discontinued at 8 weeks. Patients who have had partial or no response are treated for a full twelve weeks. Fistulae are assessed at weeks 0, 1, 2, 4, 6, 8 and 12 by physical examination scoring criteria, photography, and a subjective patient survey. CDAI is calculated at enrollment, at the start of therapy, and every other week. The Inflammatory Bowel Disease Quality of Life Survey is completed initially and at weeks four, eight, twelve, and sixteen. Follow-up is performed at week 16 with telephone follow-up monthly out to six months from the date of enrollment or up to relapse.

Inclusion Criteria

1) Age greater than or equal to 18 years old.
2) History of Crohn's disease for at least three months with extent of disease described endoscopically or radiologically within the past three years. Patients in Part B must have had previous characterization of their perianal disease (e.g., clinical exam, exam under anesthesia (EUA), magnetic resonance imaging, or CT scan).
3) Part A: Crohn's Disease Activity Index (CDAI)>200 and <450. Part B: At least 1 draining perianal and/or rectovaginal fistula, refractory to general medical management. Previously treated patients who have had a previous response or remission are eligible for retreatment if they have evidence of increased disease activity manifest by reopening of previously closed fistulas (Part B) or who have a CDAI of >220 and have an absolute increase of more than 70 from the treatment nadir (Part A).
4) If on aminosalicylate medication (Sulfasalazine, Pentasa, Asacol, Dipentum, Rowasa enemas), must be on for eight weeks and a stable dose for four weeks. If recently discontinued, must be off for at least two weeks prior to study enrollment.
5) If using oral corticosteroids, patients must have been using them for more than 8 weeks, and been on a stable dose (<20 mg/day of prednisone equivalent) for at least 4 weeks prior to trial enrollment.
6) Patients must be off antibiotics for at least two weeks, or if on antibiotics, therapy must be for at least 8 weeks and the patient must be on a stable dose for 4 weeks. Antibiotic use at any time for reasons other than Crohn's disease (e.g. urinary tract infection) is allowed.
7) If female and pre-menopausal, a negative serum beta-HCG must be obtained at the screening visit and use of one of the following forms of contraception must be documented: diaphragm, condom, cervical cap, abstinence or surgical tubal ligation. Patients must agree to use adequate birth control methods until at least 2 months after the last dose of G-CSF.
8) Negative stool tests for routine culture and sensitivity, ova and parasites, and *C. difficile* toxin.
9) Written informed consent has been obtained and patients must be able to adhere to the study visit schedule and protocol.

Exclusion Criteria

1) NSAID or ASA ingestion within two weeks of study entry.
2) GI surgery within three months of entry into study.
3) Use of azathioprine, 6-MP, methotrexate or any other immune suppressant in the previous four weeks. Use of infliximab (Remicade) within the previous 12 weeks. Use of any investigation agent (aside from G-CSF) within the previous four weeks or five half-lives of the study medication, whichever is longer.
4) Presence of an ostomy in the mucosa arm. Ostomies are allowed in the fistula arm—a modified CDAI is applied.
5) A patient with any of the following medical conditions: Liver disease with a prothrombin time >2 second prolongation, portal hypertension, severe hypertension (systolic blood pressure >200 mmHg or a diastolic blood pressure >105 mmHg), renal failure requiring dialysis or a creatinine >2.5, presence of a transplanted organ.
6) Patients with a known, clinically significant, small intestine or colonic stenosis or stricture.
7) A history of leukemia or lymphoma, or other lymphoproliferative disease, or signs and symptoms of lymphoproliferative disease such as abnormal cells on CBC, or suggestive physical exam findings of lymphadenopathy of unusual size or location.
8) Evidence of abscess or active Crohn's disease related infections in need of surgical drainage
9) Known recent substance abuse (drugs or alcohol).
10) History of gout.
11) Significant unexplained abnormalities in any of the prescreening blood work.
12) Known hypersensitivity to *E. coli*-derived proteins.

Physician Visits

New patients are screened within 14 days of initiating the medication with a history, physical and recall estimation of a Crohn's disease activity index (CDAI). If the estimated CDAI is >200 and <450, subjects have a CBC drawn, beta-HCG (if female and premenopausal) and complete a diary for 1 consecutive week within the next 14 days. The subject will return for initiation at day 0. If subject meets entry/exclusion criteria, blood is drawn for CBC, electrolytes, BUN, creatinine, liver enzymes (AST, ALT, alkaline phosphatase, bilirubin), albumin, ESR, and CRP. Instruction is provided for self-administration of the medication (subcutaneous injection). Subjects are titrated to a stable WBC response. Patients are seen and examined by a physician on weeks 0, 1, 2, 4, 6, 8, 10, 12, and for the required post treatment visit at week 16. A daily diary is completed throughout the period of administration of the medication. Telephone calls are performed monthly, starting at the conclusion of G-CSF therapy and continued through six months to assess disease activity and adverse effects. At each visit, patients are provided a sufficient supply of medication to continue administration through the next visit.

Laboratory Blood Tests

CBC are performed at screening, at the times indicated by the flow sheet during treatment, and at the scheduled visit 4 weeks after completion of therapy. A panel of serum chemistry studies (electrolytes, BUN, creatinine, liver enzymes (AST, ALT, alkaline phosphatase, bilirubin) is measured at screening, and at weeks 4, 8, 12, and 16. C-Reactive Protein (CRP) and erythrocyte sedimentation rate (ESR) are measured at week 0, 2, 4, 8, 12, and 16. Laboratory results that deviate significantly from baseline (except the WBC and alkaline phosphatase) are repeated by obtaining new samples.

ANC Response-based Dosing of G-CSF

Initial dose: 3.5 micrograms per kilogram per day SQ. Doses are based on the patient enrollment weight.

Decreases Based on HIGH ANC:

Patients with an ANC>60,000/mm$^3$ (60.0×10$^9$/L) have their dose decreased by 1.0 micrograms per kilogram per day. Otherwise, subsequent dose adjustments are made in 0.5 mcg/kg/day increments. CBC with differential are drawn in one week. Subsequent dose modifications are made as follows.
1. For a patient with an ANC>50,000/mm$^3$, the next scheduled dose is lowered by 0.5 mcg/kg/day. The ANC is rechecked in 1 week.
2. For a patient with an ANC of between 40–50,000/mm$^3$, the next scheduled dose is kept the same. The ANC is rechecked in 1 week.
3. For a patient with two consecutive ANC measurements between 40–50,000/mm$^3$, the next ANC measurement is performed at the next scheduled physician visit.

Increases Based on LOW ANC

Patients with an ANC<30,000/mm$^3$ (30.0×10$^9$/L) have their dose increased by 1.0 micrograms per kilogram per day. CBC with differential are drawn in one week. Subsequent dose modifications are made as follows.
1. For a patient with an ANC<40,000/mm$^3$, the next scheduled dose is increased by 0.5 mcg/kg/day. The ANC is rechecked in 1 week.
2. For a patient with an ANC of between 40–50,000/mm$^3$, the next scheduled dose is kept the same. The ANC is rechecked in 1 week.
3. For a patient with two consecutive ANC measurements between 40–50,000/mm$^3$, the next ANC measurement is performed at the next scheduled physician visit.

Physicians may decrease dosages as necessary due to severe bone pain. Once the ANC has been in the target range (40–50) on two consecutive measurements, monitoring is increased to the next scheduled physician visit. Physician or nurse coordinators review the CBC results and call the patient with any dosage change.

Example 4

This example shows the protocol for a further study of the method of the present invention using GM-CSF.

An open-labeled, pilot, dose escalation study of GM-CSF is performed in patients with CD. Fifteen patients are enrolled with active disease (Crohn's Disease Activity Index—CDAI>200 and <450). Patients are required not to have used steroids, azathioprine of other immune modulator for four weeks. NSAID use is not allowed for two weeks prior to or throughout the study. An open-labeled dose escalation study is conducted in three groups of five (4 mcg/kg/day; 6 mcg/kg/day; 8 mcg/kg/day) Neutrophil function is tested before the initiation of GM-CSF and at week eight (two weeks after the completion of six weeks of administration of the medication) to assess neutrophil chemotaxis and superoxide production. CBC is examined on day 0, 7 and then weekly except for week 5. C-Reactive Protein (CRP) and erythrocyte sedimentation rate (ESR) is examined every two weeks. Patients are examined weekly during the trial with telephone calls once a week as well for safety monitoring. Patients complete a daily diary throughout the study. CDAI is calculated weekly and an Inflammatory Bowel Disease Quality of Life Survey is completed at week 0, week four and week eight. Follow-up is performed at week 8, and 12 with telephone follow-up monthly for six months.

Inclusion Criteria:
1) Age over 16 years old.
2) History of Crohn's disease for at least three months with extent of disease described endoscopically or radiologically within the past two years.
3) Crohn's disease activity index>200 and <450.
4) If on a mesalamine medication (sulfasalazine, Pentasa, Asacol. Dipentum, Rowasa enemas), must be on for eight weeks and a stable dose for four weeks.
5) If on antibiotics, must be on stable doses for at least six weeks.
6) If female and pre-menopausal, a negative serum beta-HCG must be obtained at the screening visit and use of one of the following forms of contraception must be documented: diaphragm, condom, cervical cap, abstinence or surgical tubal ligation.
7) Negative stool tests for routine culture and sensitivity and *C. difficile* assay.
8) Written informed consent has been obtained.

Exclusion Criteria:
1) NSAID or ASA ingestion within two weeks of study entry.
2) GI surgery within three months of entry into study.
3) Use of steroids, azathioprine, 6-MP, methotrexate or any other immune suppressant in the previous four weeks. Use of infliximab (Remicade) within the previous 12 weeks. Use of any investigation agent within the previous four weeks or five half-lives of the study medication, whichever is longer.
4) Presence of an ostomy.
5) A patient with any of the following medical conditions: Liver disease with a prothrombin time >2 second prolongation; portal hypertension; severe hypertension (systolic blood pressure >200 mmHg or a diastolic blood pressure >105 mmHg); renal failure requiring dialysis or a creatinine >2.5.
6) Patients with a clinically significant tight small intestine or colonic stenosis or stricture.
7) A history of leukemia or lymphoma Physician Visits Subjects are screened within 14 days of initiating the medication with a history, physical and recall estimation of a Crohn's disease activity index (CDAI). If the estimated CDAI is >200 and <450, subjects have a CBC drawn, beta-HCG if female and premenopausal) and complete a diary for 1 consecutive week within the next 14 days. The subject returns for initiation at day 0. If subject meets entry/exclusion criteria, blood is drawn for CBC, BUN, creatinine, liver enzymes (AST, ALT, alkaline phosphatase, bilirubin), Albumin, ESR, CRP and neutrophil studies (see section below). Instruction is provided for self-administration of the medication (IM injection). Subject visits weekly except for week five. Visits are required at week 8 and 12. A daily diary is completed throughout the period of administration of the medication. Telephone calls are performed weekly during the medication period through week 8 and monthly through six months to assess disease activity and adverse effects. At each visit, patients are provided a sufficient supply of medication in preloaded syringes to continue administration through the next physician visit.

Dose Adjustment

Patients with an absolute neutrophil count of >30,000 have dose held for 3 days when a CBC rechecked. If the ANC is <30,000 the dose is resumed at 2 mcg/kg/day lower than the dose administered when the leukocytosis occurred.

Study Failure

Patients are considered to have failed therapy if their CDAI increases by >125 points on two separate occasions during the study or deteriorates in any way considered significantly worse by the physicians.

Assessment of Treatment Efficacy

Assessment is determined by a decrease in CDAI with remission considered a CDAI<150 and in significant improvement considered a decrease of at least 70 points. Treatment failure is considered inability to tolerate the therapy, a worsening of disease (more than 100 points) or need to use additional medication for management of Crohn's disease. IBDQ is also performed at 3 time points: at initiation of therapy at week 3 and at week 6. Note: CDAI is calculated with and without febrile episodes. As GM-CSF can induce febrile episodes, the CDAI, which includes fevers as one extra intestinal manifestation in the calculation of disease activity score, for calculating the index, is calculated with and without fevers assessed. Entry criteria are calculated including febrile episodes.

Possible Adverse Events

The principal concern is lack of effect or an exacerbation of disease. The serious toxicities reported have been associated with doses greater than 10 mcg/kg/day. Systemic symptoms were identified in 27% of patients in a review of 295 patients in phase I and phase II studies. Bone pain (21%) and fever (18%) were the most commonly reported events though these symptoms were severe in <2% of patients. Fevers can be well-managed with acetaminophen. These reactions are less common at doses proposed in this protocol. Skin reactions at sites of subcutaneous injection are usually mild or moderate and resolve on discontinuation. The range of doses to be tested here is 4–8 mcg/kg/day.

Patients receiving GM-CSF (Sargramostim) have experienced fever; chills; nausea; vomiting; diarrhea; fatigue; weakness; headache; decreased appetite; thrombosis; rapid or irregular heartbeat or other heart problems; feeling of faintness; facial flushing; pain in the bones, muscles, chest abdomen, or joints; local reaction at the site of injection; rashes; and kidney and liver dysfunction.

There have been infrequent reports of fluid accumulation or worsening of pre-existing fluid accumulation in the extremities, in the lungs, and around the heart which may result in breathing problems or heart failure. Rarely, patients have developed acute allergic reactions. There have been reports of low blood pressure, hypoxia (low oxygen), transient loss of consciousness, and difficulty in breathing after the first injection of Sargramostim. These signs may or may not recur with additional injections of Sargramostim. Patients with prior heart, lung, kidney or liver problems may have worsening of their symptoms following administration of Sargramostim. There may be other side effects that could occur.

The invention claimed is:

1. A method of treating pouchitis comprising:
    administering to a patient with pouchitis an immune stimulatory amount of an agonist of CD116 (Granulocyte-Macrophage Colony Stimulating Factor Receptor (GM-CSFR)), wherein the agonist of CD116 is selected from the group consisting of GM-CSF, human GM-CSF, human GM-CSF produced in yeast, and sargramostim.

2. The method of claim 1 wherein the agonist is sargramostim.

3. The method of claim 1 wherein the agonist is made in yeast.

4. The method of claim 1 wherein the agonist is human GM-CSF.

5. A method of reducing the risk of fistula recurrence, comprising:
    administering to a patient with Crohn's disease who has previously had a fistula, with an immune stimulatory amount of an agonist of CD116 (Granulocyte-Macrophage Colony Stimulating Factor Receptor (GM-CSFR)), wherein the agonist of CD116 is selected from the group consisting of GM-CSF, human GM-CSF, human GM-CSF produced in yeast, and sargramostim, whereby the risk of recurrence of a fistula is reduced.

6. The method of claim 5 wherein the agonist is sargramostim.

7. The method of claim 5 wherein the agonist is made in yeast.

8. The method of claim 5 wherein the agonist is human GM-CSF.

9. The method of claim 1 or 5 wherein the agonist is GM-CSF.

10. A method of treating Ulcerative Colitis comprising:
    administering to a patient with Ulcerative Colitis an immune stimulatory amount of an agonist of CD116 (Granulocyte-Macrophage Colony Stimulating Factor Receptor (GM-CSFR)), wherein the agonist of CD116 is selected from the group consisting of GM-CSF, human GM-CSF, human GM-CSF produced in yeast, and sargramostim.

11. The method of claim 10 wherein the patient has mucosal inflammatory disease of at least one of the small intestine, colon, or rectum, and the amount of agonist administered is sufficient to reduce the mucosal inflammation.

12. The method of claim 10 wherein the amount of agonist administered is sufficient to induce remission of the mucosal disease.

13. The method of claim 10 wherein the patient has epithelial damage of at least one of the small intestine, colon, or rectum, and the amount of agonist administered is sufficient to repair the epithelial damage.

14. The method of claim 10 wherein the amount of agonist administered is sufficient to reduce the patient's symptoms.

15. The method of claim 10 wherein the patient is in remission.

16. The method of claim 10 wherein the patient has received surgical therapy of affected portions of the gastrointestinal tract.

17. The method of claim 10 the agonist is GM-CSF.

18. The method of claim 10 wherein the agonist is sargramostim.

19. The method of claim 10 wherein the agonist is made in yeast.

20. The method of claim 10 wherein the agonist is human GM-CSF.

* * * * *